United States Patent [19]

Breipohl et al.

[11] Patent Number: 6,046,306

[45] Date of Patent: Apr. 4, 2000

[54] PNA SYNTHESIS USING AN AMINO PROTECTING GROUP WHICH IS LABILE TO WEAK ACIDS

[75] Inventors: Gerhard Breipohl, Frankfurt; Eugen Uhlmann, Glashütten, both of Germany

[73] Assignee: Hoechst Aktiengesellschaft, Frankfurt am Main, Germany

[21] Appl. No.: 08/927,178

[22] Filed: Sep. 11, 1997

Related U.S. Application Data

[63] Continuation of application No. 08/402,385, Mar. 13, 1995, abandoned.

[30] Foreign Application Priority Data

Mar. 14, 1994 [DE] Germany .............................. 44 08 531

[51] Int. Cl.$^7$ .............................. C07K 1/04; C07N 21/00
[52] U.S. Cl. .......................... 530/322; 530/334; 530/335; 536/25.3; 536/89
[58] Field of Search ..................................... 530/322, 334, 530/335; 536/25.3, 89

[56] References Cited

U.S. PATENT DOCUMENTS 5,015,733  5/1991  Smim et al. .
5,367,066  11/1994  Urdea et al. .

FOREIGN PATENT DOCUMENTS 93307455  9/1993  United Kingdom .

*Primary Examiner*—Bennett Cels
*Attorney, Agent, or Firm*—Finnegan, Henderson, Farabow, Garrett & Dunner, L.L.P.

[57] ABSTRACT

PNA synthesis using an amino protective group which is labile to weak acids.

5 Claims, No Drawings

PNA SYNTHESIS USING AN AMINO PROTECTING GROUP WHICH IS LABILE TO WEAK ACIDS

This is a continuation of application Ser. No.08/402,385, filed Mar. 13, 1995 now abandoned.

Peptide or polyamide nucleic acids (PNAs) are DNA-analogous compounds in which the deoxyribose phosphate backbone has been replaced by a peptide oligomer. To temporarily protect the amino group of the monomer, the syntheses hitherto described in the literature (Michael Egholm, Peter E. Nielsen, Ole Buchardt and Rolf H. Berg, J. Am. Chem. Soc. 1992, 114, 9677–9678; Ole Buchardt, Michael Egholm, Peter E. Nielsen and Rolf H. Berg, WO 92/20702) use the acid-labile tert-butyloxycarbonyl (Boc) protective group which is cleared off by medium-strong acids, such as, for example, trifluoroacetic acid. The solid-phase synthesis of oligomers is carried out analogously to the customary peptide synthesis process as it has been described by, for example, Merrifield (B. Merrifield, J. Am. Chem. Soc., 1963, 85, 2149). The PNA oligomer is cleared off from the solid carrier using a strong acid, customarily liquid hydrogen fluoride. The repeated treatment with trifluoroacetic acid and the subsequent cleavage using halogen fluoride is not compatible with the synthesis of mixed PNA/DNA sequences since the nucleosidic linkage is not stable under these conditions. In particular, the purine nucleotides deoxyguanosine and deoxyadenosine are rapidly cleaved by strong acids at the N-glycosidic linkage. It would, furthermore, be particularly desirable, for synthesizing such molecules, to use the customary DNA synthesizers and to retain to a large extent, the chemistry used in this equipment.

It is the aim of the invention to develop a synthesis process for the construction of the PNA oligomers using a temporary amino protective group which is labile to weak acids, which process permits the oligomer to be cleaved off from the solid support under the alkaline conditions conventionally used for oligonucleotides.

The invention which follows describes a process for the preparation of PNA oligomers of the formula I

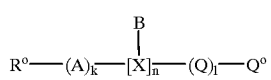

in which
B/X is

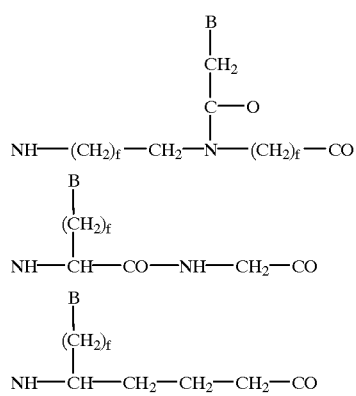

-continued

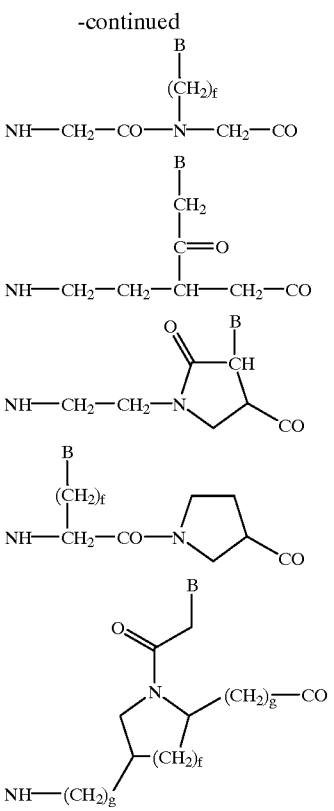

preferably

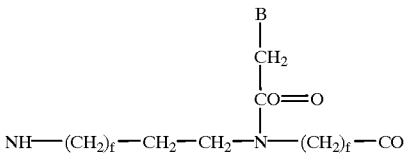

where f is 1–4, preferably 1 or 2, and g is 0–3, preferably 0–2, $R^0$ is hydrogen, $C_1$–$C_{18}$-alkanoyl, $C_1$–$C_{18}$-alkoxycarbonyl, $C_3$–$C_8$-cycloalkanoyl, $C_7$–$C_{15}$-aroyl, $C_3$–$C_{13}$-heteroaroyl, or a group which favors intracellular uptake of the oligomer or interacts with the terget uncleic acid during hybridazation;

A is an amino acid radical, preferably from the series consisting of glycine, leucine, histidine, phenylalanine, cysteine, lysine, arginine, aspartic acid, glutamic acid, proline, tetrahydroisoquinoline-3-carboxylic acid, octahydroindole-2-carboxylic acid and N-(2-aminoethyl) glycine;

k is an integer from zero to 10, preferably zero to 6;

Q is an amino acid radical, preferably from the series consisting of glycine, leucine, histidine, phenylalanine, cysteine, lysine, arginine, aspartic acid, glutamic acid, proline, tetrahydroisoquinoline-3-carboxylic acid, octahydroindole-2-carboxylic acid and N-(2-aminoethyl) glycine;

l is an integer from zero to 10, preferably zero to 6;

B is a nucleotide base customary in nucleotide chemistry, for example natural nucleotide bases such as adenine, cytosine, guanine, thymine and uracil, or unnatural nucleotide bases, such purine, 2,6-diaminopurine, 7-deazaadenine, 7-deazaguanine, $N^4N^4$-ethanocytosine, $N^6N^6$-ethano-2,6-diaminopurine, 5-methylcytosine, 5-($C_3$–$C_6$)-alkynyluracil, 5-($C_3$–$C_6$)-alkynylcytosine, 5-fluorouracil or pseudoiso-cytosine, 2-hydroxy-5-methyl-4-triazolopyrimidine, or their prodrug forms, or else base substitute compounds such as, for example imidazole, nitro-imidazole and triazole;

$Q^0$ is hydroxyl, $NH_2$ or $NHR''$, in which $R''$ is $C_1$–$C_{18}$-alkyl, $C_2$–$C_{18}$-aminoalkyl or $C_2$–$C_{18}$-hydroxyalkyl; and n is an integer from 1–50, preferably 4–35, which comprises a) either firstly coupling amino acids (Q') onto a polymeric support of the formula II L-[polymer]   (II), which is provided with an anchoring group L which is latently provided with the radical Q, using a process conventionally used in solid-phase synthesis, b) if appropriate cleaving off the protective group PG which is labile to weak acids, using a suitable reagent, c) repeating steps a and b (1—1) times, d) and coupling onto the compound of the formula III, which is formed as an intermediate (Q')$_l$-L-[polymer]   (III), in which L is as defined above, Q' is an amino acid Q which is optionally protected in the side chain, and l is an integer from zero to 10, a compound of the formula IV

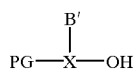   (IV)

in which

PG is an amino protective group which is labile to weak acids and

B'/X is a unit as defined in formula I, provided with a nucleotide base which is optionally protected on the exocyclic amino or hydroxy function, in which B' are bases conventionally used in nucleotide chemistry, for example natural bases such as adenine, cytosine, guanine, thymine and uracil, or unnatural bases, such as purine, 2,6-diaminopurine, 7-deazaadenine, 7-deazaguanine, $N^4N^4$ ethanocytosine, $N^6N^6$-ethano-2,6-diaminopurine, 5-methylcytosine, 5-($C_3$–$C_6$)-alkynyl-uracil, 5- ($C_3$–$C_6$) -alkynylcytosine, 5-fluorouracil or pseudoisocytosine, the exocyclic amino or hydroxyl groups of these optionally being protected by suitable, known protective groups, such as the benzoyl, isobutanoyl, acetyl, phenoxyacetyl, 4-(t-butyl)benzoyl, 4-(t-butyl)phenoxyacetyl, 4-(methoxy)benzoyl, 2-(4-nitrophenyl)ethyloxycarbonyl, 2-(2,4-dinitrophenyl)ethyloxycarbonyl, 9-fluorenylmethoxycarbonyl, diphenylcarbamoyl or formamidine group, preferably the benzoyl, isobutanoyl, 4-(t-butyl) benzoyl, 2-(4-nitrophenyl)ethyl-oxycarbonyl, 2-(2,4-dinitrophenyl)ethyloxycarbonyl, 9-fluorenylmethoxycarbonyl group, and, in the case of guanine, by a combination of 2-N-acetyl with the 6-O-diphenylcarbamoyl group, or else are base substitute compounds such as, for example, imidazole, nitro-imidazole and triazole, or else coupling a compound of the formula IV directly onto the polymeric support of the formula II, using the coupling reagents conventionally used in peptide chemistry, e) cleaving off the temporary protective group PG which is labile to weak acids by means of a suitable reagent, f) repeating steps d and e (n-1) times, g) coupling on further amino acids (A') using a process conventionally used in solid-phase synthesis, h) cleaving off the protective group PG which is labile to weak acids by means of a suitable reagent, i) repeating steps g and h (k-1) times, j) in the event that $R^0$ is not hydrogen, introducing the radical $R^0$ using a customary process, and k) cleaving off the compound of the formula I from the polymeric support out of the compound of the formula Ia obtained as intermediate

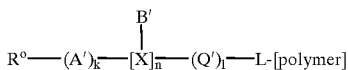   (Ia)

in which $R^0$, k, B'/X, n, Q'' and l are as defined above, A' is an amino acid A which is optionally protected in the side chain and L is an anchoring group, using a cleaving reagent, during which process the protective groups which are optionally present on the exocyclic amino or hydroxyl function of the nucleotide bases and on the side chains of the amino acids are simultaneously or else subsequently cleaved off.

The synthesis scheme for PNA shown hereinbelow shows the course of this process:

[L]-[polymer]

↓ a) PG—(Q')—OH is coupled on

PG—(Q')—[L-[polymer]

↓ b) protective group PG is cleaved off

H—(Q')—[L]—[polymer]

↓ c) steps a and b are repeated (1—1) times

H—(Q')$_l$—[L]-[polymer]

↓ d) PG—[B'/X]—OH is coupled on

PG—[B'/X]—(Q')$_l$—[L]-[polymer]

↓ e) protective group PG is cleaved off

H—[B'/X]—(Q')$_l$—[L]—[polymer]

↓ f) steps d and e are repeated (n-1) times

H—[B'/X]$_n$—(Q')$_l$—[L]—[polymer]

↓ g) PG—(A')—OH is coupled on

PG—(A')—[B'/X]$_n$—(Q')$_l$—[L]—[polymer]

↓ h) protective group PG is cleaved off

H—(A')—[B'/X]$_n$—(Q')$_l$—[L]—[polymer]

↓ i) steps g and h are repeated (k-1) times

H—(A')$_k$—[B'/X]$_n$—(Q')—[L]—[polymer]

↓ j) group $R^0$ is coupled on $R^0$—(A')$_k$—[B'/X]$_n$—(Q')$_l$—[L]—[polymer]

↓ k) polymer and protective groups are cleaved off $R^0$—(A)$_k$—[B/X]$_n$—(Q)$_l$—$Q^0$ Groups which favor intracellular uptake of the oligomer are, for example, alkanoyl and alkoxycarbonyl compounds having a variety of lipophilic radicals such as —$(CH_2)_x$—$CH_3$ in which x is a integer from 6–18, —$(CH_2)_n$—$CH=CH$—$(CH_2)_m$—$CH_3$ in which n and m independently of one another are an integer from 6 to 12, —$(CH_2CH_2O)_4$—$(CH_2)_9$—$CH_3$, —$(CH_2CH_2O)_8$—$(CH_2)_{13}$—$CH_3$ and —$(CH_2CH_2O)_7$—$(CH_2)_{15}$—$CH_3$, but also steroid radicals such as cholesteryl, or vitamin radicals such as vitamin E, vitamin A or vitamin D, and other conjugates which make use of natural carrier systems, such as bile acid, folic acid, 2-(N-alkyl, N-alkoxy)aminoanthraquinone and conjugates of mannose and peptides of the corresponding receptors which result in receptor-mediated endocytosis of the oligomers, such as EGF (epidermal growth factor), bradykinin and PDGF (platelet derived growth factor). Labeling groups are to be understood as meaning fluorescent groups, for example of dansyl (N-dimethyl-1-aminonaphthyl-5-sulfonyl), fluorescein or coumarin derivatives, or chemiluminescent groups, for example of acridine derivatives, as well as the digoxygenin system which can be detected via ELISA, the biotin group, which can be detected via the biotin/avidin system, or else linker arms having functional groups which allow derivatization at a later point in time with detectable reporter groups, for example an aminoalkyl linker which is reacted with an acridinium active ester to give a chemiluminescence probe. Typical labeling groups are:

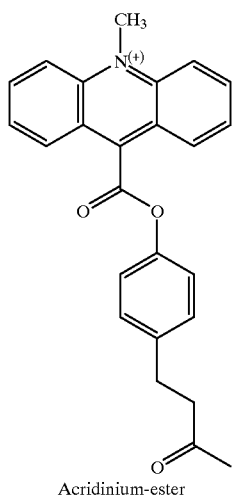

Acridinium-ester

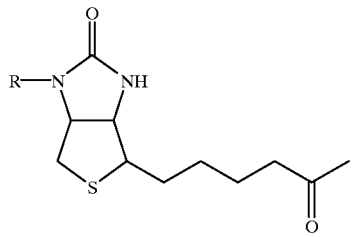

Biotin conjugate ( = "biotin" for R = Boc)
R = H or amino protective group

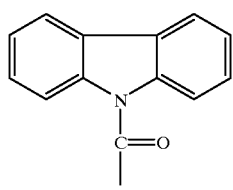

Carbazole derivative

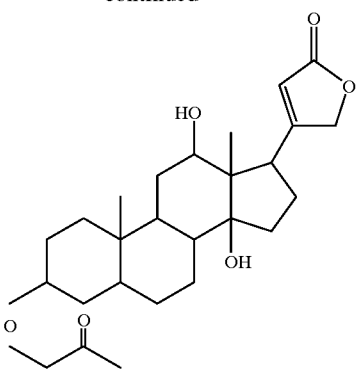

Digoxigenin conjugate groups which upon hybridazotion of the oligomer with the target nucleic attack the latter by binding, crosslinking or cleaving are for example, acridine, psoralene, phenanthridine, naphthoquinone, daunomycin or chloroethylaminoaryl conjugates. Typical intercalating and crosslinking radicals are:

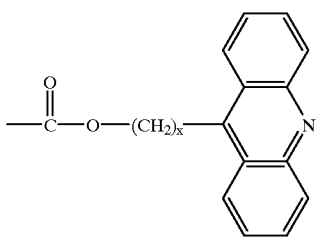

Acridine derivative $x = 2$–$12$, preferably 4

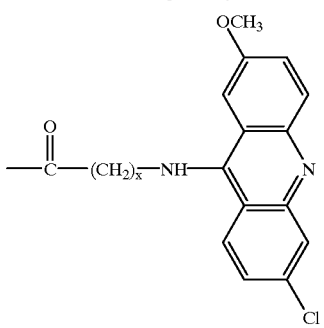

$x = 2$–$12$, preferably 4

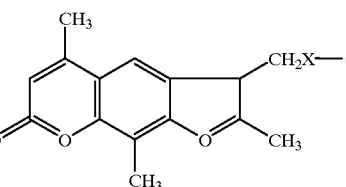

Trimethylpsoralene conjugate ( = "psoralene" for $x = O$)
X = ——NH— or ——O——

-continued

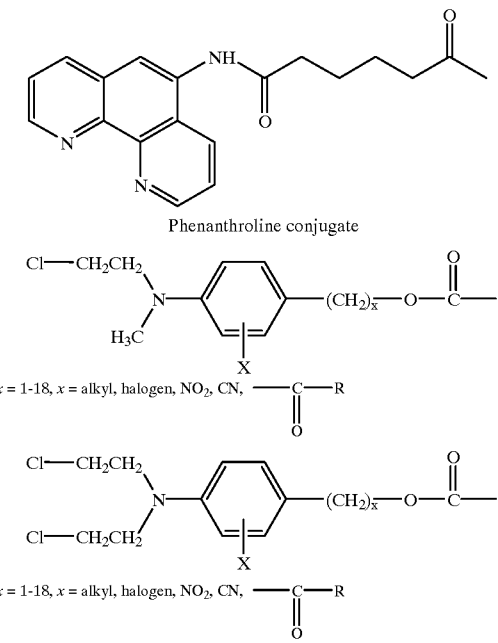

Phenanthroline conjugate $x = 1-18$, $x$ = alkyl, halogen, $NO_2$, CN,  —C(=O)—R $x = 1-18$, $x$ = alkyl, halogen, $NO_2$, CN,  —C(=O)—R Anchoring groups L which latently contain the function $Q^0$ are, for example described by George Barany, Nancy Kneib-Cordonier and Daniel G. Mullen., Int. J. Peptide Protein Res., 1987, 30, 705–739.

Polymeric supports which are provided with an anchoring group and which latently contain the group $Q^0$ are, for example, p-nitrobenzophenoneoxime/polystyrene resin (E. T. Kaiser, B. H. Nakagawa, J. Org. Chem. 1983, 48, 678–685), 4-(2-hydroxyethylsulfonyl)benzoyl resin, or the polymeric supports which are functionalized with a primary amino group, such as, for example, ®polyHIPE, ®Tentagel, ®Controlled Pore Glass, polystyrene onto which there is coupled one of the anchoring groups which latently contain the group $Q^0$, such as, for example, 4-hydroxymethylbenzoic acid (E. Atherton, C. J. Logan, R. C. Sheppard, J. Chem. Soc., Perkin Trans. I, 538–546 (1981)), 9-hydroxymethylfluorene-4-carboxylic acid (M. Mutter, D. Bellof, Helv. Chim. Acta 67, 2009–2016 (1984)), 4-(2-hydroxyethylsulfonyl)benzoic acid (R. Schwyzer, E. Felder, P. Failli, Helv. Chim. Acta 67, 1316–1327 (1984)); (9-(hydroxymethyl)-2-fluorenylacetic acid (Y. Z. Liu, S. H. Ding, J. Y. Chu, A. M. Felix, Int. J. Peptide Protein Res. 35, 95–98 (1990)), N-[9-(hydroxymethyl)-2-fluorenyl]succinic monoamide; 4-(2-hydroxyethyl)-3-nitrobenzoic acid (F. Albericio, E. Giralt, R. Eritia, Tetrahedron Lett. 1991, 1515–1518), mono (amino-$C_2$–$C_{16}$) alkyl succinates, mono (amino-$C_2$–$C_{16}$)alkyl oxalates and the like.

The following anchoring groups, or anchoring groups which are already linked with the polymeric supports, are preferably used:

p-nitrobenzophenoneoxime/polystyrene resin, 4-(2-hydroxyethylsulfonyl)benzoyl resin, or the anchoring groups which latently contain the group $Q^0$ too and which are coupled onto Tentagel, Controlled Pore Glass or polystyrene type carriers functionalized with a primary amino group, such as 4-hydroxymethylbenzoic acid, 4-(2-hydroxyethylsulfonyl)benzoic acid, N-[9-(hydroxymethyl)-2-fluorenyl]succinic monoamide, mono (amino-$C_2$–$C_{16}$) alkyl succinates or mono(amino-$C_2$–$C_{16}$)alkyl oxalates.

Examples of protective groups PG which are labile to weak acids are 1-(1-adamantyl)1-methylethoxycarbonyl (Adpoc), 1-(3,5-di-tert-butylphenyl)-1-methylethoxycarbonyl, (t-Bumeoc), 1-methyl-1-(4-biphenyl)ethyloxycarbonyl (Bpoc), 3,5-dimethoxyphenyl-2-propyl-2-oxycarbonyl (Ddz) or those of trityl type such as triphenylmethyl (Trt), (4-methoxyphenyl)diphenylmethyl (Mmt), (4-methylphenyl)diphenylmethyl (Mtt), di-(4-methoxyphenyl)phenylmethyl (Dmt) and 9-(9-phenyl)xanthenyl (pixyl), trityl type protective groups, such as Trt, Mmt and Dmt, being particularly preferably used, and the Mmt protective group being very particularly preferably used.

The activating methods conventionally used in peptide synthesis which are used in step a of the above synthesis process are described, for example, in Houben-Weyl, Methoden der organischen Chemie [Methods in Organic Chemistry], volume 15/2, Georg Thieme Verlag Stuttgart 1974, and further reagents such as, for example, BOP (B. Castro, J. R. Dormoy, G. Evin and C. Selve, Tetrahedron Lett. 1975, 1219–1222), PyBOP (J. Coste, D. Le-Nguyen and B. Castro, Tetrahedron Lett. 1990, 205–208), BroP (J. Coste, M.-N. Dufour, A. Pantaloni and B. Castro, Tetrahedron Lett. 1990, 669–672), PyBroP (J. Coste, E. Frerot, P. Jouin and B. Castro, Tetrahedron Lett. 1991, 1967–1970) and uronium reagents such as, for example, HBTU (V. Dourtoglou, B. Gross, V. Lambropoulou, C. Zioudrou, Synthesis 1984, 572–574), TBTU, TPTU, TSTU, TNTU, (R. Knorr, A. Trzeciak, W. Bannwarth and D. Gillessen, Tetrahedron Letters 1989, 1927–1930), TOTU (EP-A-0 460 446), HATU (L. A. Carpino, J. Am. Chem. Soc. 1993, 115, 4397–4398), HAPyU, TAPipU (A. Ehrlich, S. Rothemund, M. Brudel, M. Beyermann, L. A. Carpino and M. Bienert, Tetrahedron Lett. 1993, 4781–4784), BOI (K. Akaji, N. Kuriyama, T. Kimura, Y. Fujiwara and Y. Kiso, Tetrahedron Lett. 1992, 3177–3180) or 2,4,6-mesitylenesulfonyl-3-nitro-1,2,4-triazolide (MSNT) (B. Blankemeyer-Menge, M. Nimitz and R. Frank, Tetrahedron Lett. 1990, 1701–1704), 2,5-diphenyl-2,3-dihydro-3-oxo-4-hydrothiophene dioxide (TDO) (R. Kirstgen, R. C. Sheppard, W. Steglich, J. Chem. Soc. Chem. Commun. 1987, 1870–1871) or activated esters (D. Hudson) Peptide Res. 1990, 51–55) are described in the references in question.

The use of carbodiimides, for example dicyclohexylcarbodiimide or diisopropylcarbodiimide, is preferred. Phosphonium reagents such as, for example, PyBOP or PyBroP, and uronium reagents such as, for example, HBTU, TBTU, TPTU, TSTU, TNTU, TOTU, HATU or BOI, are also preferably used.

Coupling can be effected directly by subjecting amino acid derivative or PNA monomer of the formula IV to an addition reaction with the activating reagent, if appropriate with an addition of additives such as, for example, 1-hydroxybenzotriazole (ROBt) (W. König, R. Geiger, Chem. Ber. 103, 788 (1970)) or 3-hydroxy-4-oxo-3,4-dihydrobenzotriazine (Hoobt) (W. König, R. Geiger, Chem. Ber. 103, 2034 (1970)) to the resin, or else the unit may be preactivated separately, giving an activated ester, and the solution of the activated species in a suitable solvent added to the polymer capable of being coupled.

Protective groups which are compatible with the amino protective group PG which is labile to weak acids are used as the protective group for the exocyclic amino function of the protected nucleotide base B'. Protective groups which are preferably used are the benzoyl, isobutanoyl, acetyl, phenoxyacetyl, 4-(t-butyl)benzoyl, 4-(t-butyl)phenoxyacetyl, 4-(methoxy)benzoyl, 2-(4-nitrophenyl)ethyloxycarbonyl, 2-(2,4-dinitrophenyl)ethyloxycarbonyl, 9-fluorenylmethoxycarbonyl, diphenylcarbamoyl or formamidine group. Particularly preferred are the benzoyl, isobutanoyl, 4-(t-butyl)benzoyl, 2-(4-nitrophenyl)ethyloxycarbonyl, 2-(2,4-dinitrophenyl)ethyloxycarbonyl, 9-fluorenylmethoxycarbonyl, 4-(methoxy)benzoyl or para-(t-butyl)phenoxyacetyl, para-nitrophenyl-2-ethyloxycarbonyl group and, in the case of guanine, a combination of the 2-N-acetyl with the 6-O-diphenylcarbamoyl group.

Examples of cleaving reagents for the amino protective group PG which is labile to weak acids are a solution of 1–10% of trifluoroacetic acid in dichloromethane, a solution of 1–10% of trichloroacetic acid in dichloromethane, a solution of 2–15% of dichloroacetic acid in dichloromethane or 1–5% of p-toluenesulfonic acid in dichloromethane. Other suitable cleaving reagents are Lewis acids, such as, for example boron trifluoride etherate or zinc bromide in dichloromethane/isopropanol.

The amino acid radicals Q' or A' of the formula Ia are coupled on by means of amino acid derivatives which preferably have the same amino protective group PG which is also used for the compounds of the formula IV. Any side-chain functions which may be present on the amino acids are provided with protective groups which are labile to bases or alkali metal hydroxide solution, such as, for example, 9-fluorenylmethyl (Fm) or 9-fluorenylmethoxycarbonyl (Fmoc). Preferred are amino acid derivatives such as PG-Gly-OH, PG-Tic-OH, PG-Pro-OH, PG-Phe-OH, PG-Oic-OH, PG-Lys(Fmoc)-OH, PG-Arg(Fmoc)-OH, PG-Cys(Pm)-OH, PG-Asp(OPm)-OH, PG-Glu(OFm)-OH and PG-Aeg(Fmoc)-OH, PG-His(Trb)-OH, in which PG is as above. Very particularly preferred here are the following amino acid derivatives: Mmt-Gly-OH, Mmt-Tic-OH, Mmt-Pro-OH, Mmt-Phe-OH, Mmt-Oic-OH, Mmt-Lys(Fmoc)-OH, Mmt-Arg(Fmoc)-OH, Mmt-Cys(Fm)-OH, Mmt-Asp(OPm)-OH, Mmt-Glu(OFm)-OH and Mmt-Aeg(Fmoc)-OH, Mmt-His(Fmoc)-OH.

The preparation of the compounds of the formula IV

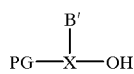

(IV)

especially as

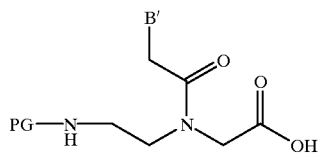

which are employed in the above-described synthesis process is described in a simultaneously filed patent application titled Substituted N-ethylglycine derivatives for preparing PNA and PNA/DNA hybrids (HOE 94/F 058, DE-A44 08 534).

The above-described PNAs are constructed by solid-phase synthesis on a suitable support material (for example polystyrene, polyoxyethylene-modified polystyrene, such as, for example, ®Tentagel, ®Controlled Pore Glass), which is provided with an anchoring group L which latently contains the radical $Q^0$. Solid-phase synthesis starts at the C-terminal end of the PNA by coupling a monomer which is protected by an acid-labile protective group or an amino acid which is optionally protected in the side-chain function onto a suitable resin.

After the protective group of the unit coupled onto the resin has been cleaved off using a suitable reagent, as described above, the subsequent protected units (PNA monomers and amino acid derivatives) are coupled on one after the other in the sequence desired. The PNA resins protected N-terminally by an acid-labile protective group which are formed as intermediates are deblocked by the above-described reagents before they are linked with the subsequent PNA monomer.

Coupling or activating the amino acid derivatives with one of the abovementioned activating reagents can be carried out in dimethylformamide, N-methylpyrrolidinone, acetonitrile or methylene chloride, or a mixture of the abovementioned solvents. The previously mentioned solvents can additionally also be treated with auxiliary bases such as, for example, pyridine, N-ethylmorpholine or triethylamine. The activated derivative is conventionally employed in a 1.5 to 10 fold excess. In cases, in which coupling is incomplete, the coupling reaction is repeated without deblocking the amino group of the unit which has just been coupled on.

Processes for introducing the radical $R^0$ are, for example in the event that this radical contains a carboxylic acid function, the methods described above for coupling on the amino acids and PNA monomers. Other processes are the reaction of isocyanates such as, for example, phenyl isocyanate, isothiocyanates such as, for example, fluorescein isothiocyanate, chloroformic acid derivatives such as, for example, chloroformylcarbazole, active esters of carbonic acid such as, for example, cholesterol-(4-nitrophenyl) carbonate, acridinium succinimidyl carbonate, sulfonyl chlorides such as, for example, dansyl chloride, and the like.

If appropriate, the amino and carboxyl terminus of the compounds of the formula I can also be linked to each other in a further step. This linkage is preferably effected via an amide linkage between the side-chain functions of the amino acid radicals A or Q, A and Q being Lys, Glu, Asp, Aeg, or by forming a disulfide bridge between in each case one amino acid A and Q. A and Q being Cys.

The synthetis sequence described hereinabove can also be carried out by means of commercially available automatic synthesizers such as, for example, peptide synthesizers, multiple peptide synthesizers and DNA synthesizers, with a slight modification of the conventionally used synthetis programmes.

After the PNAs have been synthesized in the manner described above, the PNA oligomer can be cleaved off from the resin using suitable reagents such as, for example, concentrated ammonia solution, ethylenediamine, hydrazine, butylamine, methylamine or ethanolamine. Depending on the linker used and the nature of the protective groups used, the oligomer and the other sidechain protective groups of the nucleic bases are cleaved off simultaneously. The cleaving reagent can also be used diluted with suitable solvents, such as, for example, acetonitrile, ethanol or methanol.

Purification of the crude oligomer obtained after the cleavage is effected by processes conventionally used in peptide or nucleotide chemistry, such as, for example, HPLC, ion exchange chromatography and the like.

The abbreviations used for amino acids correspond to the three-letter code as described in Europ. J. Biochem. 138, 9 (1984) which is conventionally used in peptide chemistry.

Other abbreviations used are listed hereinbelow.

| | |
|---|---|
| Aeg | N-(2-Aminoethyl) glycyl, —NH—CH$_2$—CH$_2$—NH—CH$_2$—CO— |
| Aeg(A$^{MeOBz}$) | N-(2-Aminoethyl)-N-((9-(N$^6$-4-methoxybenzoyl)-adenosyl)acetyl)glycyl |
| Aeg(C$^{Bz}$) | N-(2-Aminoethyl)-N-((1-(N$^4$benzoyl)-cytosyl)acetyl)glycyl |
| Aeg(C$^{MeOBz}$) | N-(2-Aminoethyl)-N-((1-(N$^4$-4-methoxybenzoyl)cytosyl)acetyl)glycyl |
| Aeg (C$^{tBuBz}$) | N-(2-Aminoethyl)-N-((1-(N$^4$-4-tert-butylbenzoyl)cytosyl)acetyl)glycyl |
| Aeg(G$^{iBu}$) | N-(2-Aminoethyl)-N-((9-(N$^2$-isobutanoyl)-guanosyl)acetyl)glycyl |
| Aeg(G$^{2-Ac,\ 4-Dpc}$) | N-(2-Aminoethyl)-N-((9-(N$^2$-acetyl-O$^4$-diphenylcarbamoyl)guanosyl)glycyl |
| Aeg(T) | N-(2-Aminoethyl)-N-((1-thyminyl)acetyl)-glycyl |
| Bnpeoc | 2,2[Bis(4-nitrophenyl)]ethoxycarbonyl) |
| Boc | tert-Butyloxycarbonyl |
| BOI | 2-(Benzotriazol-1-yl)oxy-1,3-dimethyl-imidazolidinium hexafluorophosphate |
| BOP | Benzotriazolyl-1-oxy-tris(dimethylamino)-phosphonium hexafluorophosphate |
| BroP | Bromotris(dimethylamino)phosphonium hexafluorophosphate |
| BSA | N,O-Bis(trimethylsilyl)acetamide |
| But | tert-Butyl |
| Bz | Benzoyl |
| Bzl | Benzyl |
| Cl-Z | 4-Chlorobenzyloxycarbonyl |
| CPG | Controlled Pore Glass |
| DBU | 1,8-Diazabicyclo[5.4.0]undec-7-ene(1,5-5) |
| DCM | Dichloromethane |
| Ddz | 3,5-Dimethoxyphenyl-2-propyl-2-oxy-carbonyl |
| DMF | Dimethylformamide |
| Dmt | Di-(4-methoxyphenyl)phenylmethyl |
| Dnpeoc | 2-(2,4-Dinitrophenyl)ethoxycarbonyl |
| Dpc | Diphenylcarbamoyl |
| FAM | Fluorescein radical |
| Fm | 9-Fluorenylmethyl |
| Fmoc | 9-Fluorenylmethyloxycarbonyl |
| H-Aeg-OH | N-(2-Aminoethyl)glycine |
| HAPyU | O-(7-Azabenzotriazol-1-yl)-1,1,3,3-bis-(tetramethylene)uronium hexafluorophosphate |
| HATU | O-(7-Azabenzotriazol-1-yl)-1,1,3,3-tetramethyluronium hexafluorophosphate |
| HBTU | O-(Benzotriazol-1-yl)-1,1,3,3-tetramethyluronium hexafluorophosphate |
| HOBt | 1-Hydroxybenzotriazole |
| HONSu | N-Hydroxysuccinimide |
| HOObt | 3-Hydroxy-4-oxo-3,4-dihydrobenzotriazine |
| iBu | Isobutanoyl |
| MeOBz | 4-Methoxybenzoyl |
| Mmt | 4-Methoxytriphenylmethyl |
| Moz | 4-Methoxybenzyloxycarbonyl |
| MSNT | 2,4,6-Mesitylenesulfonyl-3-nitro-1,2,4-triazolide |
| Mtt | 4-Methylphenyl)diphenylmethyl |
| NBA | Nitrobenzyl alcohol |
| NMP | N-Methylpyrrolidine |
| Pixyl | 9-(9-Phenyl)xanthenyl |
| PyBOP | Benxotriazolyl-1-oxy-tripyrrolidino-phosphonium hexafluorophosphate |
| PyBroP | Bromotripyrrolidinophosphonium hexafluorophosphate |
| TAPipU | O-(7-Azabenzotriazol-1-yl)-1,1,3,3-bis-(pentamethylene)uronium tetrafluoroborate |
| TBTU | O-(Benzotriazol-1-yl)-1,1,3,3-tetramethyluronium tetrafluoroborate |
| tBu | tert-Butyl |
| tBuBz | 4-tert-Butylbenzoyl |
| TDBTU | O-(3,4-Dihydro-4-oxo-1,2,3-benzotriazin-3-yl)-1,1,3,3-tetramethyluronium tetrafluoroborate |
| TDO | 2,5-Diphenyl-2,3-dihydro-3-oxo-4-hydroxy-thiophene dioxide |
| TFA | Trifluoroacetic acid |
| THF | Tetrahydrofuran |
| TNTU | O-[(5-Norbonene-2,3-dicarboximido]-1,1,3,3-tetramethyluronium tetrafluoroborate |
| TOTU | O-[(Cyano(ethoxycarbonyl)methylene)-amino]-1,1,3,3-tetramethyluronium tetrafluoroborate |
| TPTU | O-(1,2-dihydro-2-oxo-1-pyridyl)-1,1,3,3'-tetramethyluronium tetrafluoroborate |
| Trt | Trityl |
| TSTU | O-(N-Succinimidyl)-1,1,3,3-tetramethyl-uronium tetrafluoroborate |
| Z | Benzyloxycarbonyl |
| MS(ES$^+$) | Electrostatic spray mass spectrum (positive ion) |
| MS(ES$^-$) | Electrostatic spray mass spectrum (negative ion) |
| MS(DCI) | Desorption chemical ionization mass spectrum |
| MS(FAB) | fast atom bombardment mass spectrum |

The examples which follow are intended to illustrate the preferred methods for the preparation of the compounds according to the invention, without limiting the invention thereto.

Synthesis of the peptide nucleic acids

The PNAs are synthesized for example using a Ecosyn D-300 DNA Synthesizer (Eppendorf/Biotronik, Maintal) or an ABI 380B DNA Synthesizer (Applied Biosystems, Weitersstadt). The synthetis cycles are described herein below.

Synthesis is effected in standard DNA synthesis columns from Applied Biosystems packed with Mmt-hex-succ-Tentagel or Mmt-hex-succ-CPG. Columns for syntheses on a 3 μmol or 6 μmol scale are used. The reagent used for cleaving off the Mmt protective group is 3% of trichloroacetic acid in dichloromethane. After the carrier has been washed with acetonitrile, neutralization is effected using a 3.5 M solution of 4-ethylmorpholine in acetonitrile. For the coupling, a mixture composed of an 0.3 or 0.4 M solution of the Mmt-Aeg derivatives in acetonitrile/DMF, DMF/NMP with 1% of Triton X-100, DMF with N-ethylmorpholine, DMF with pyridine, an 0.9 M solution of PyBOP in acetonitrile and a 3.5 M solution of 4-ethylmorpholine in acetonitrile or an 0.3 M solution of HATU in DMF with an 0.3 M solution of NEM in DMF is introduced into the synthetis column. Subsequent capping is effected using a 1:1 mixture of the standard DNA synthesis capping reagent (acetic anhydride/lutidine/N-methylimidazole solution in THP). The PNA is treated on the synthesizer with concentrated ammonia solution and so cleaved off from the carrier, the combined ammoniacal solutions being heated for 5 hours at 55° C. in a sealed ampoule to remove the base protective groups. If appropriate, this is then followed by cleaving off the aminoterminal Mmt group using 80% acetic acid at room temperature.

The PNAs are analyzed using a Beckman System Gold HPLC apparatus equipped with a Dionex Nucleopac PA-100 (4×250 mm) column with a linear gradient of 0–0.75H NaCl in 20 mM NaOR.

Purification is effected in a Pharmacia Biopilot FPLC apparatus equipped with a Pharmacia Mono Q HR 10/10 column with a linear gradient of 0–0.5M NaCl in 20 M NaOH as the eluent. The salts are removed from the purified PNAs with the aid of a BondElut-C18 column (Analytichem Int'l) or using ®Biogel (Biorad).

EXAMPLE 1

1-Hydroxy-6-((4-methoxyphenyl)diphenylmethylamino)hexate (Mmt-hex)

6-Aminohexan-1-ol (1 g; 8.55 mmol) is dissolved in anhydrous pyridine (7 ml), and triethylamine (0.2 ml) is added. To this solution there is added in the course of 45 minutes a solution of (4-methoxyphenyl)diphenylmethyl chloride (2.5 g; 8.12 mmol) in anhydrous pyridine (9 ml). Stirring of the reaction solution is continued for 30 minutes at 22° C. and quenched by adding methanol (3 ml). The solution is concentrated on a rotary evaporator, and the residue obtained is coevaporated three times with toluene to remove the pyridine. The residue obtained is dissolved in ethyl acetate, and this solution is washed in succession with a saturated sodium bicarbonate solution, water and a saturated potassium chloride solution. After the organic phase has been dried over $Na_2SO_4$ it is filtered and the solution is concentrated in vacuo. The crude product can be purified by silica gel chromatography using heptane:ethyl acetate:triethylamine/49.5:49.5:1. Yield: 1.64 g MS (FAB, NBA/LiCl) 396.3 $(M+Li)^+$, 390.3 $(M+H)^+$, 273.2 $(MMT)^+$ $R_f$ 0.44 (heptane:ethyl acetate=1:1).

EXAMPLE 2

6-((4-Methoxyphenyl)diphenylmethylamino)hex-1-y 1 hemisuccinate (Mmt-hex-succ)

1-Hydroxy-6-((4-methoxyphenyl)diphenylmethylamino)-hexane (1.00 g; 2.57 mmol) is dissolved in anhydrous pyridine (10 ml). To this solution there are added succinic anhydride (0.257 g; 2.57 mmol) and 4-dimethylaminopyridine (31.3 mg; 0.257 mmol). After the mixture has been stirred for 3 hours at 22° C., more succinic anhydride (25.7 mg; 0.257 mmol) and 4,4-dimethylaminopyridine (62.6 mg; 0.56 mmol) are added, and this solution is heated for 6 hours at 50° C. After a further 16 hours at 22° C., the mixture is concentrated, the residue is taken up in ethyl acetate, and the solution obtained is washed with ice-cold 5% aqueous citric acid. After the organic phase has been dried ($Na_2SO_4$), the solution is concentrated on a rotary evaporator. Purification of the residue by silica gel chromatography using 50% $CH_2Cl_2$/1% triethylamine in ethyl acetate and then using 5% methanol/1% triethylamin in dichloromethane gives the desired compound in the form of a colorless oil. MS ($ES^-$) 978.0 $(2M-H)^-$, 488.3 $(M-H)^-$ $R_f$ 0.30 ($CH_2Cl_2$:ethyl acetate=1:1).

EXAMPLE 3

6-((4-Methoxyphenyl)diphenylmethylamino)hex-1-yl-succinylamido-Tentagel (Mmt-hex-succ-Tentagel)

The amino form of Tentagel$^R$ (Rapp Polymere) (0.5 g; 0.11 mmol of amino groups) is allowed to swell for 10 minutes in 4-ethylmorpholine (0.1 ml) and DMF (5 ml). A solution of 6-((4-methoxyphenyl)diphenylmethylamino)hex-1-yl hemisuccinate (97.4 mg; 0.165 mmol), 4-ethylmorpholine (15.9 mg; 0.138 mmol; 17.4 ml) and TBTU (52.9 mg; 0.165 mmol) in DMP (3 ml) is then added and the suspension is shaken for 16 hours at 22° C. The derivatized Tentagel carrier is filtered off, washed in succession with DMF (3×3 ml), $CH_2Cl_2$ (3×1 ml) and diethyl ether (3×1 ml) and dried. Unreacted amino functions are blocked by a 1-hour treatment with acetic anhydride/lutidine/1-methylimidazole in THF (1 ml). The finished carrier is washed with $CH_2Cl_2$ (3×1 ml) and diethyl ether (3×1 ml) and dried in vacuo. The loading based on the monomethoxytrityl function introduced is 168 $\mu$molg$^{-1}$.

EXAMPLE 4

6-((4-Methoxyphenyl)diphenylmethylamino)hex-1-y 1 succinylamidopropyl-Controlled Pore Glass (Mmt-hex-succ-CPG)

The preparation is carried out analogously to the procedure described in Example 3, starting from aminopropyl-CPG (Fluka) (550 Å; 1.0 g) and 6-((4-methoxyphenyl)diphenylmethylamino)hex-1-yl hemisuccinate (48.7 mg; 0.082 mmol), 4-ethylmorpholine (7.6 ml) and TBTU (26.4 mg; 0.082 mmol) in DMF (3 ml). The loading of the MMT-hex-succCPG is 91 $\mu$molg$^1$.

EXAMPLE 5

H-[Aeg(T)]$_3$-(hex)

H-[Aeg(T)]$_3$-(hex) is synthesized on the 3 $\mu$mol scale on Mmt-Hex-Succ-Tentagel by the above-described synthesis processes. The monomer used is Mmt-Aeg(T)-OH. The crude yield is 71 OD$_{260}$. The mass spectrum recorded of 2 OD shows the desired product at m/e 915.8 $(M+H)^+$, and, as the by-product, H-[Aeg(T)]$_2$-(hex) at m/e 650.5.

EXAMPLE 6

H-[Aeg(T)]-[Aeg(C)]-[Aeg(T)]-[Aeg(C)]-[Aeg(T)]$_2$-(hex)

H-[Aeg(T)]-[Aeg(C)]-[Aeg(T)]-[Aeg(C)]-[Aeg(T)]$_2$-(hex) is synthesized on a 3 $\mu$mol scale on Mmt-Rex-Succ-Tentagel by above-described synthetis processes. The monomers used are Mmt-Aeg(T)-OH and Mmt-Aeg($C^{Bz}$)-OH. The crude yield is 98.6 OD$_{260}$. 35 OD$_{260}$ of the crude product are purified and the salt is removed, giving 14.5 OD$_{260}$ of the desired compound. Mass spectrometry analysis of the purified product shows the desired product m/e 1685.0 $(M+H)^+$ as a single main peak.

EXAMPLE 7

H-[Aeg(T)]-[Aeg(c)]-[Aeg(T)]-Aeg(c)]-[Aeg(T) 2-(hex)

H-[Aeg(T)]-[Aeg(C)]-[Aeg(T)]-Aeg(C)]-[Aeg(T)]$_2$-(hex) is synthesized on the 3 $\mu$mol scale on Mmt-Hex-Succ-Tentagel by above-described synthesis processes. The monomers used are Mmt-Aeg(T)-OH and Mmt-Aeg($C^{tBuBz}$)-OH.

EXAMPLE 8

H-[Aeg(A)]-[Aeg(C)]-[Aeg(A)]-[Aeg(T)]-[Aeg(C)]-[Aeg(A)]-[Aeg(T)]-[Aeg(G)]-[Aeg(G)]-[Aeg(T)]-[Aeg(C)]-[Aeg(G) (hex)

The PNAs are synthesized using a Ecosyn D-300 DNA synthesizer (Eppendorf/Maintal) on 130 mg (5 $\mu$Mol) of Mmt-Rex-Succ-aminopropyl-CPG. Fcr the following solutions were employed in the synthesis:

| | |
|---|---|
| 1) Activator solution: | 0.3 molar HATU solution in dried DMF |
| 2) Base for activation: | 0.3 molar solution of NEM in dried DMF |
| 3) Cleaving off Mmt | 3% solution of trichloroacetic acid in dichloromethane |
| 4) Neutralization solution | Tetrahydrofuran/water/pyridine 7:2:1 |
| 5) Mmt-Aeg(T)-OH: | 0.3 molar solution in 0.3 molar solution of NEM in dried DMF |
| 6) Mmt-Aeg(A$^{MeOBz}$)-OH: | 0.3 molar solution in 0.3 molar solution of NEM in dried DMF |
| 7) Mmt-Aeg(C$^{MeOBz}$)-OH: | 0.3 molar solution in 0.3 molar solution of NEM in dried DMF |
| 8) Mmt-Aeg(G$^{iBu}$)-OH: | 0.3 molar solution in 0.3 molar solution of NEM in dried DMF. |

When the synthesis has ended, the PNA-CPG carrier is dried and worked up as described above. Yield: 245 OD$_{260}$ MS 3369.6(ES$^+$): (M)$^+$.

We claim:

1. A process for the preparation of PNA oligomers of the formula

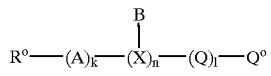

(I)

in which

B-X is

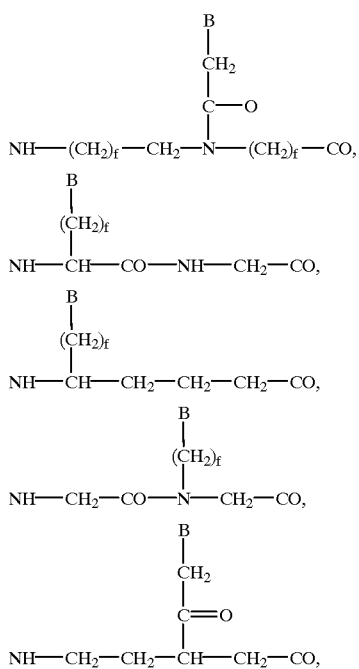

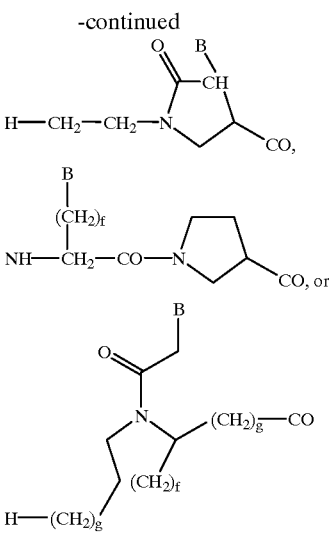

-continued where f is 1–4 and g is 0–3;

R$^0$ is hydrogen, C$_1$–C$_{18}$-alkanoyl, C$_1$–C$_{18}$-alkoxycarbonyl, C$_3$–C$_8$-cycloalkanoyl, C$_7$–C$_{15}$-aroyl, C$_3$–C$_{13}$-heteroaroyl, or a group which favors intracellular uptake of the oligomer;

A is an amino acid radical;

k is an integer from zero to 10;

Q is an amino acid radical;

l is an integer from zero to 10;

B is a natural nucleotide base or unnatural nucleotide base conventionally used in nucleotide chemistry or their prodrug forms, or a base substitute compound;

Q$^0$ is hydroxyl, NH$_2$ or NHR", in which R" is C$_1$–C$_{18}$-alkyl, C$_2$–C$_{18}$-aminoalkyl or C$_2$–C$_{18}$-hydroxyalkyl; and n is an integer from 1–50, which comprises a) optionally first coupling 0–10 amino acids PG-(Q')-OH, wherein Q' is an amino acid radical Q which is optionally protected in the side chain by a protective group PG' and PG is an amino protective group labile to weak acids, selected from the group consisting of 1- (1-adamantyl)1-methylethoxycarbonyl (Adpoc), 1- (3,5-di-tert-butylphenyl)-1-methylethoxycarbonyl (t-Bumeoc), 1-methyl-1-(4-biphenyl)-ethyloxycarbonyl (Bpoc), 3,5-dimethoxyphenyl-2-propyl-2-oxycarbonyl (Ddz) a trityl group (4-methoxyphenyl)diphenylmethyl (Mmt), (4-methylphenyl)diphenylmethyl (Mtt), di-(4-methoxyphenyl)phenylmethyl (Dmt) and 9-(9-phenyl)xanthenyl (pixyl), onto a polymeric support of the formula II L-{polymer}   (II), which is provided with an anchoring group L which is latently provided with the radical Q$^0$, using a process conventionally used in solid-phase synthesis, b) if appropriate, cleaving off said protective group PG, using a suitable reagent, c) optionally repeating steps a and b (l–1) times, d) and coupling onto the compound of the formula III,

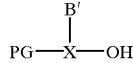  (III), in which L, Q' and I are as defined above, a compound of the formula IV (IV)

PG—X—OH
    |
    B' in which

PG is an amino protective group which is labile to weak acids and B'-X is a unit as defined in formula 1, provided with a nucleotide base which is optionally protected on the exocyclic amino or hydroxy function in which B' are natural bases or unnatural bases conventionally used in nucleotide chemistry whose exocyclic amino or hydroxyl groups are optionally protected by suitable known protective groups PG", or if a) is not performed, coupling a compound of the formula IV directly onto the polymeric support of the formula II, using the coupling reagents conventionally used in peptide chemistry, e) cleaving off said temporary protective group PG by means of a suitable reagent, f) repeating steps d and e (n−1) times, g) optionally coupling on further k amino acids PG-(A')-OH, wherein k is an integer from zero to 10, A' is an amino acid radical A which is optionally protected in the side chain by a protective group PG" and PG is an amino protective group which is labile to weak acids, using a process conventionally used in solid-phase synthesis, h) cleaving off said protective group PG by means of a suitable reagent, i) optionally repeating steps g and h (k−1) times, j) in the event that $R^0$ is not hydrogen, introducing the radical $R^0$ using a customary process, and k) cleaving off the compound of the formula I under alkaline conditions from the polymeric support out of the compound of the formula Ia obtained as intermediate

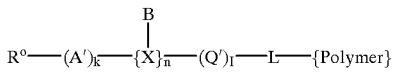  (Ia)

in which $R^0$, k, B'-X, n, Q', A', L and I are as define above, using a cleaving reagent, during which process the protective groups PG' and PG", which are optionally present on the exocyclic amino or hydroxyl function of the nucleotide bases and on the side chains of the amino acids, are simultaneously or else subsequently cleaved off.

2. A process for the preparation of PNA oligomers of the formula I as claimed in claim 1, wherein A is an amino acid radical selected from the group consisting of glycine, leucine, histidine, phenylalanine, cysteine, lysine, arginine, aspartic acid, glutamic acid, proline, tetrahydroisoquinoline-3-carboxylic acid, octahydroindole-2-carboxylic acid and N-(2-aminoethyl)glycine;

k is an integer from zero to 6;

Q is an amino acid radical selected from the group consisting of glycine, leucine, histidine, phenylalanine, cysteine, lysine, arginine, aspartic acid, glutamic acid, proline, tetrahydroisoquinoline-3-carboxylic acid, octahydroindole-2-carboxylic acid and N-(2-aminoethyl)glycine;

l is an integer from zero to 6;

B is a natural nucleotide base selected from the group consisting of adenine, cytosine, guanine, thymine and uracil, or an unnatural nucleotide base, selected from the group consisting of purine, 2,6-diaminopurine, 7-deazaadenine, 7-deazaguanine, $N^4N^4$-ethanocytosine, $N^6N^6$-ethano-2,6-diaminopurine, 5-methylcytosine, S-($C_3$–$C_6$)alkynyluracil, 5-($C_3$–$C_6$) alkynylcytosine, 5-fluorouracil pseudoisocytosine, 2-hydroxy-5-methyl-4-triazolopyrimidine, or their prodrug forms, or is imidazole, nitroimidazole or triazole; and n is an integer from 4–35.

3. The process of claim 1 wherein PG is a triphenylmethyl (Trt).

4. The process of claim 1 wherein PG is (4-methoxylphenyl)-diphenylmethyl (Mmt).

5. The process of claim 2 wherein PG is a triphenylmethyl (Trt).

* * * * *

UNITED STATES PATENT AND TRADEMARK OFFICE
CERTIFICATE OF CORRECTION

PATENT NO. : 6,046,306
DATED : April 4, 2000
INVENTOR(S) : Gerhard Breipohl, et al Page 1 of 2

It is certified that error appears in the above-indentified patent and that said Letters Patent is hereby corrected as shown below:

Claim 1, Column 16, Line 51, after "(Ddz)", insert --,--.

Claim 1, Column 15, Line 51, after "trityl group", insert --,--.

Claim 1, Column 17, Line 15, "formula 1" should read --formula I--.

Claim 1, Column 18, in formula (Ia) at the top of the column, "$(Q')_I$" should read --$(Q')_l$--.

Claim 1, Column 18, Line 7, "define" should read --defined--.

Claim 2, Column 18, Line 30, after "base", delete ",".

Claim 2, Column 18, Line 34, "S-$(C_3-C_6)$alkynyluracil" should read --5-$(C_3-C_6)$alkynyluracil--.

Claim 2, Column 18, Line 35, after "5-fluorouracil", insert --,--.

Claim 2, Column 18, Line 36, "or their" should read --and their--.

UNITED STATES PATENT AND TRADEMARK OFFICE
CERTIFICATE OF CORRECTION

| | | |
|---|---|---|
| PATENT NO. | : | 6,046,306 |
| DATED | : | April 4, 2000 |
| INVENTOR(S) | : | Gerhard Breipohi, et al |

It is certified that error appears in the above-indentified patent and that said Letters Patent is hereby corrected as shown below:

Claim 3, Column 18, Line 40, before "triphenylmethyl", delete "a".

Claim 5, Column 18, Line 44, before "triphenylmethyl", delete "a".

Signed and Sealed this

Thirteenth Day of March, 2001

*Attest:*

NICHOLAS P. GODICI

*Attesting Officer*    *Acting Director of the United States Patent and Trademark Office*